United States Patent [19]
Kirschbaum

[11] Patent Number: 5,644,642
[45] Date of Patent: Jul. 1, 1997

[54] GAZE TRACKING USING OPTICAL COHERENCE TOMOGRAPHY

[75] Inventor: Alan R. Kirschbaum, Oakland, Calif.

[73] Assignee: Carl Zeiss, Inc., Thornwood, N.Y.

[21] Appl. No.: 415,678

[22] Filed: Apr. 3, 1995

[51] Int. Cl.⁶ ............................................. G06K 9/00
[52] U.S. Cl. .................................... 382/103; 382/131
[58] Field of Search ............................. 382/100, 103, 382/117, 131, 190, 291; 348/78; 351/206, 210, 211

[56] References Cited

U.S. PATENT DOCUMENTS

| | | | |
|---|---|---|---|
| 4,836,670 | 6/1989 | Hutchinson | 351/210 |
| 4,950,069 | 8/1990 | Hutchinson | 351/210 |
| 5,036,347 | 7/1991 | Tsunekawa et al. | 354/400 |
| 5,204,703 | 4/1993 | Hutchinson et al. | 351/210 |
| 5,214,455 | 5/1993 | Penney et al. | 351/210 |
| 5,220,361 | 6/1993 | Lehmer et al. | 351/226 |
| 5,231,674 | 7/1993 | Cleveland et al. | 382/6 |
| 5,416,317 | 5/1995 | Nishimura et al. | 250/221 |
| 5,481,622 | 1/1996 | Gerhardt et al. | 382/103 |
| 5,491,757 | 2/1996 | Lehmer et al. | 382/128 |

OTHER PUBLICATIONS

"Methods & Designs Survey of eye movement recording methods" by L. R. Young and D. Sheena, *Behavior Research Methods & Instrumentation*, 1975, vol. 7(5), pp. 397–429.

"Eye Movement Analysis System Using Fundus Images" by H. Kawai, S. Tamura, K. Kani, and K. Kariya, *Pattern Recognition*, vol. 19, No. 1, 1986, pp. 77–83.

"Optical Coherence Tomography" by Huang et al., published in *Science*, 254, Nov. 22, 1991, pp. 1178–1181.

"Micron–Resolution Imaging of the Anterior Eye in Vivo with Optical Coherence Tomography" by J. A. Izatt, M. R. Hee, E. A. Swanson, C. P. Lin, D. Huang, J. S. Schuman, C. A. Puliafito, and J. G. Fujimoto, 1994, pp. 1–24.

"Micron–Resolution Ranging of Cornea Anterior Chamber by Optical Reflectometry" by D. Huang J. Wang, C. P. Lin, C. A. Puliafito, and J. G. Fujimoto, *Lasers in Surgery and Medicine*, vol. 11, 1991, pp. 419–425.

"Measurement of the axial eye length and retinal thickness by laser Doppler interferometry (LDI)" by C. K. Hitzenberger, A. F. Fercher, and M. Juchem, *SPIE vol. 1423 Opthalmic Technologies*, 1991, pp. 46–50.

"Measurement of corneal thickness by low–coherence interferometry" by C. K. Hitzenberger, *Applied Optics*, vol. 31, No. 31, Nov. 1, 992, pp. 6637–6642.

*Primary Examiner*—Andrew Johns
*Attorney, Agent, or Firm*—Michael B. Einschlag

[57] ABSTRACT

Apparatus for gaze tracking an eye utilizing short coherence length interferometry, also known as optical coherence tomography ("OCT"). An embodiment of the present invention is an apparatus for gaze tracking an eye which includes: (a) an optical coherence tomography (OCT) apparatus; (b) a scanning apparatus for scanning across a predetermined portion of the eye with optical output from the OCT apparatus; (c) an analysis apparatus for analyzing detection signals output from the OCT apparatus to determine a location of a feature of the eye; (d) an illumination apparatus for producing a reflection of radiation from a cornea of the eye (corneal reflex); (e) a detection apparatus for determining a location of the corneal reflex; and (f) the analysis apparatus further includes an apparatus which is responsive to the location of the feature and to the location of the corneal reflex for gaze tracking.

20 Claims, 3 Drawing Sheets

GAZE TRACKING USING OPTICAL COHERENCE TOMOGRAPHY

TECHNICAL FIELD OF THE INVENTION

The present invention relates to method and apparatus for gaze tracking using short coherence length interferometry (also referred to as optical coherence tomography).

BACKGROUND OF THE INVENTION

The most commonly used methods in the prior art for gaze tracking an eye (also referred to as measuring or monitoring the fixation direction of the eye) entail: (a) illuminating the eye using one of two methods and (b) acquiring and processing a video image of the illuminated pupil. In the first method of illuminating the eye, known as the "bright-pupil method," a light source is positioned so that it is nearly coaxial with respect to a line between a video camera and the eye. As a result, the pupil appears in the video image to be brightly lit. In the second method of illuminating the eye, known as the "dark-pupil method," the light source is positioned so that it is substantially off-axis with respect to the line between the video camera and the eye. As a result, the pupil appears in the video image to be dark when compared with the iris and other surrounding features. When using either of these two methods of illuminating the eye, another source of light, a point source, is located at a distance that is large when compared with the radius of curvature of the cornea. An image of the point source of light (referred to in the art as a corneal reflex) appears in the video image as a bright spot in the region of the pupil.

As is well known in the art, if the eye rotates, both the corneal reflex and the pupil move, but at different rates, whereas, if the eye merely translates, both the corneal reflex and the pupil move at the same rate. Thus, the relative distance between the corneal reflex and the center of the pupil is a measure of rotation angle or fixation angle of the eye. As a consequence of this, the most commonly used methods in the prior art for gaze tracking of the eye (measuring or monitoring the fixation direction of the eye) entail finding the center of the pupil. Typically, this is done by locating several points on the pupil/iris boundary and using straightforward geometry to determine the center of the pupil.

Since the corneal reflex is extremely bright and small, it is a straightforward matter to locate it. However, problems are frequently encountered in determining the center of the pupil. In the bright-pupil method, difficulties arise if the pupil is small. In such a case, the illuminated pupil will be rather dim and the contrast between the pupil and the iris will be low because the brightness of the pupil varies inversely as the square of the pupil diameter. Further difficulties arise in the bright-pupil method if the eye requires substantial refractive correction. In such a case, the brightness distribution in the pupil will be nonuniform, which nonuniformity creates problems in locating the pupil edges. In the dark-pupil method, difficulties arise if the contrast is low. Such low contrast occurs, for example, if the cornea or the lens act as diffuse scatters due to natural aging of tissues or the presence of cataracts. Further, depending on the wavelength of the illumination and natural pigment variations, the brightness of the iris may be naturally low. In either case, the pupil/iris contrast may be too low to determine the center of the pupil accurately.

A less frequently used method of gaze tracking the eye (monitoring or measuring the fixation direction of the eye) requires imaging features on the fundus of the eye, for example, the papilla (nerve head) or a distinctive pattern of blood vessels. Difficulties arise in this method because of cloudiness of the ocular media.

All of the above-described prior art methods rely on feature discrimination which arises from differential brightness of reflected light. However, these prior art methods make no distinction between reflected light originating from a structure of interest and reflected light originating from all scattering centers anterior to the structure of interest. This ambiguity results in loss of information. Furthermore, information about axial location of scatterers, i.e., depth of scatterers in the eye, is either nonexistent, or at best (using stereo optics) is difficult to extract.

In light of the above, there is a need for a method and apparatus for gaze tracking the eye which overcome the above-described problems in the prior art.

SUMMARY OF THE INVENTION

Advantageously, embodiments of the present invention provide a method and apparatus for gaze tracking an eye utilizing short coherence length interferometry, also known as optical coherence tomography ("OCT"), which overcome the above-described problems in the prior art. In particular, an embodiment of the present invention is an apparatus for gaze tracking an eye which comprises: (a) an optical coherence tomography (OCT) apparatus; (b) scanning means for scanning across a predetermined portion of the eye with optical output from the OCT apparatus; (c) analysis means for analyzing detection signals output from the OCT apparatus to determine a location of a feature of the eye; (d) illumination means for producing a reflection of radiation from a cornea of the eye (corneal reflex); (e) detecting means for determining a location of the corneal reflex; and (f) the analysis means further comprising means, responsive to the location of the feature and to the location of the corneal reflex, for gaze tracking.

As will be set forth in detail below, OCT advantageously solves many of the problems described in the Background of the Invention because it discriminates on the basis of both reflection and axial location. Thus, structures differing in depth by at least a few tens of microns may be distinguished, even if their reflectances are similar. As a consequence, even in the case of a severe cataract, it is possible to locate the pupil/iris boundary. Also, corneal scattering and scattering in the aqueous (except very near the pupil) does not affect the depth discrimination.

DETAILED DESCRIPTION

Figure 1:
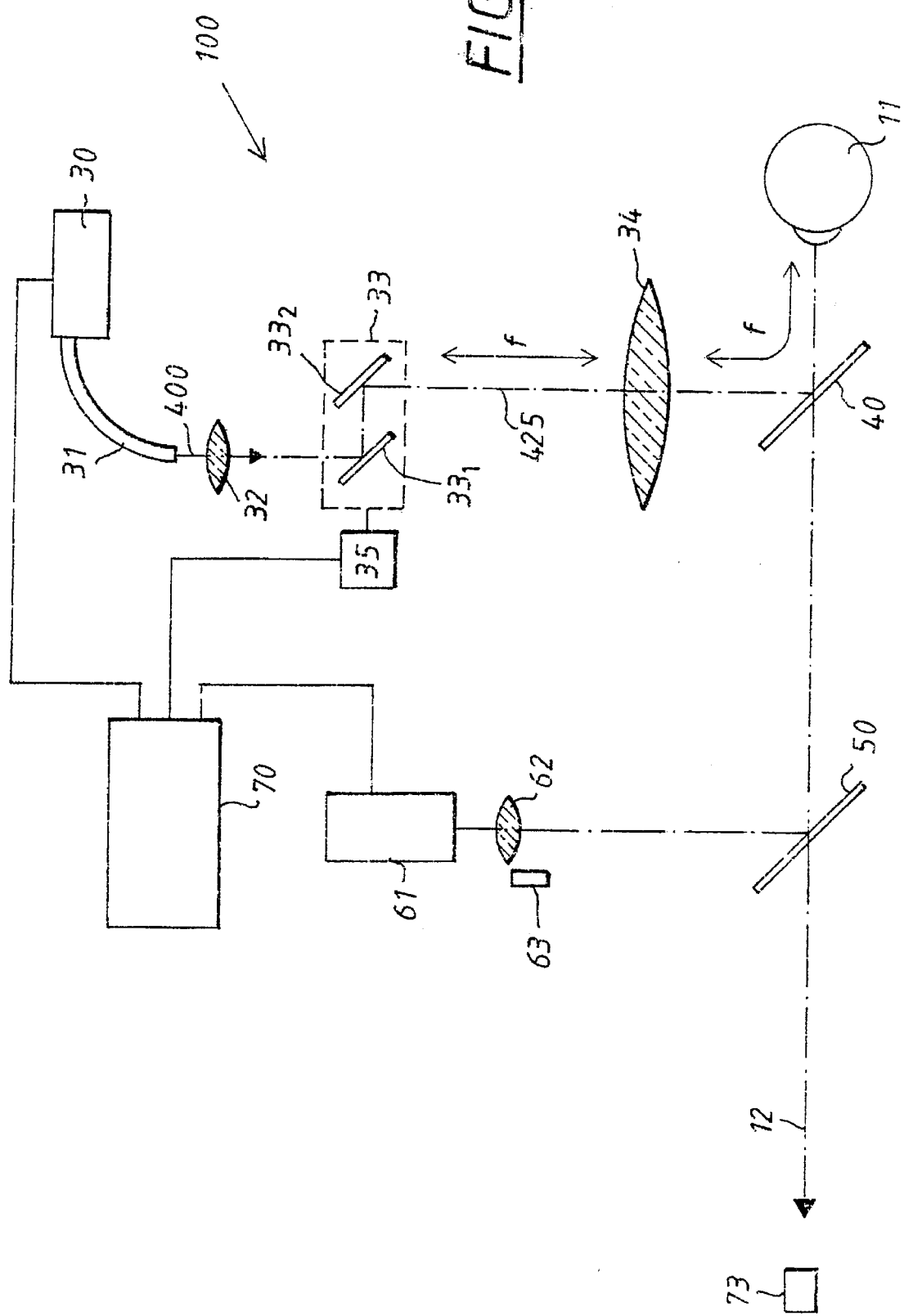
FIG. 1 shows, in pictorial form, an embodiment of a gaze tracking apparatus which is fabricated in accordance with the present invention, which embodiment includes an optical coherence tomography ("OCT") apparatus.

FIG. 1 shows, in pictorial form, an embodiment of gaze tracking apparatus 100 which is fabricated in accordance with the present invention. As shown in FIG. 1, gaze tracking apparatus 100 comprises optical coherence tomography apparatus 30 ("OCT apparatus 30"), OCT apparatus 30 will be discussed in detail below in conjunction with FIG. 4.

As shown in FIG. 1, OCT radiation 400 is output from optical fiber 31 of OCT apparatus 30. In accordance with the present invention, OCT radiation 400 has a short temporal coherence length and is substantially spatially coherent. As further shown in FIG. 1, OCT radiation 400 output from optical fiber 31 is collimated by lens 32 and the collimated radiation is input to scanner 33. As shown in FIG. 1, scanner 33 comprises scanning mirrors $33_1$ and $33_2$ which are orthogonally mounted (having orthogonal axes of rotation), galvanometer driven, scanning mirrors. Scanning mirrors $33_1$ and $33_2$ are mounted on a pair of motors (not shown), which pair of motors are operated under the control of computer 70 through scanner electronics 35 in a manner which is well known to those of ordinary skill in the art. Since the mirrors are orthogonally mounted, any two-dimensional scan path can be generated by driving each motor with an appropriate voltage waveform. OCT radiation 425 is output from scanner 33 and is focused by scanning lens 34. In accordance with the present invention, scanning lens 34 has a focal length f and, as shown in FIG. 1, scanner 33 is placed substantially in the back focal plane of scanning lens 34. OCT radiation 425 is focused by scanning lens 34 and is reflected by beamsplitter 40 towards eye 11. In accordance with the present invention, and as will be described below, OCT radiation 425 is comprised of wavelengths substantially in the near infrared and, as a result, beamsplitter 40 is fabricated in accordance with methods which are well known to those of ordinary skill in the art to be reflective in the near infrared.

As is well known to those of ordinary skill in the art, scanner 33 and scanning lens 34, under control of computer 70, cause a focused spot of OCT radiation to scan (traverse a predetermined trajectory across) the plane of the pupil of eye 11. As is also well known, the OCT radiation is reflected from eye 11 and the reflected OCT radiation is transmitted back along the path described above to OCT apparatus 30. Finally, output from OCT apparatus 30 is applied as input to computer 70 for analysis to determine the center of the pupil of eye 11.

Figure 2A:
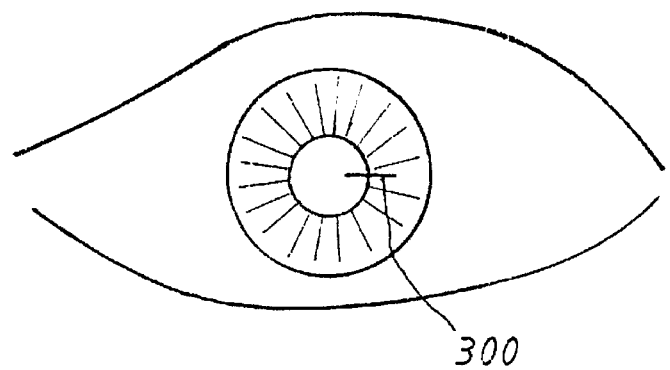
FIG. 2A shows, in pictorial form, a front view of an eye which illustrates a scan of OCT radiation across the pupil/iris boundary of the eye.
Figure 2B:
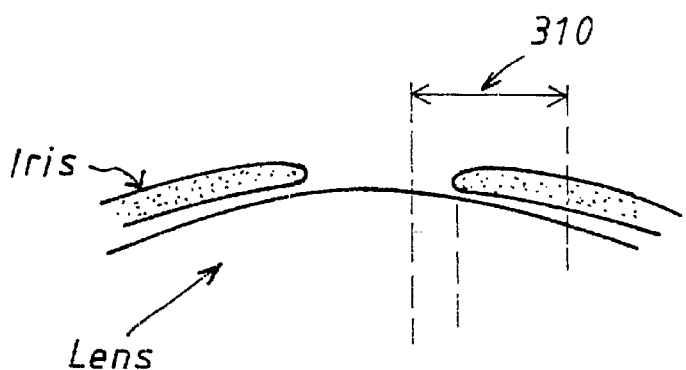
FIG. 2B shows, in pictorial form, a cross section of the eye which illustrates the scan of the OCT radiation across the pupil/iris boundary of the eye.
Figure 2C:
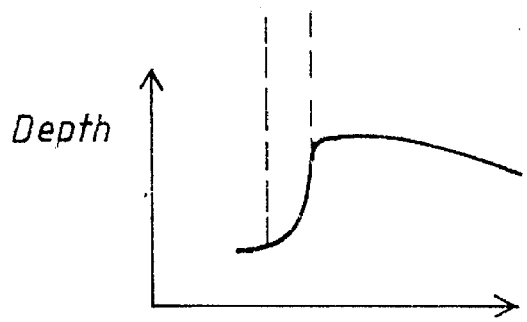
FIG. 2C shows, in graphical form, a plot of depth for an OCT output signal exceeding a predetermined amplitude as a function of distance along the scan of the OCT radiation across the pupil/iris boundary of the eye.

The following, in conjunction with FIGS. 2A-2C, describes the analysis performed by computer 70 to determine the center of the pupil of eye 11. In accordance with the present invention, as has been described above, a point source of OCT radiation is scanned transversely across a structure of interest, for example, the pupil/iris boundary of eye 11. FIG. 2A shows a front view of eye 11 which illustrates a scan of OCT radiation across the pupil/iris boundary of eye 11 and line 300 in FIG. 2A represents the scan-path of the OCT radiation across the pupil/iris boundary. FIG. 2B shows a cross section of eye 11 and line 310 in FIG. 2B represents the scan-path of the OCT radiation across the pupil/iris boundary. Finally, FIG. 2C shows, in graphical form, a plot of depth for an OCT output signal exceeding a predetermined amplitude as a function of distance along the scan of the OCT radiation across the pupil/iris boundary. As is known, in accordance with the principles of OCT, OCT radiation is reflected from all scatterers along the path of the OCT radiation in the axial direction, i.e., a direction into eye 11. In OCT apparatus 30, the OCT radiation reflected from eye 11 interferes with OCT radiation from a reference path within OCT apparatus 30. The length of the reference path is varied periodically and the length of the reference path is known accurately (see the description of OCT apparatus 30 which is provided below in conjunction with FIG. 4). As is well known, the OCT output signal from OCT apparatus 30 is generated only when the length of the path of the OCT radiation reflected from features of eye 11 is equal to the length of the reference path (to within a length corresponding to the OCT radiation temporal coherence length). Thus, the depth of features of eye 11 can be determined at all depths in the axial direction at a given point in the transverse scan. As one can readily appreciate from FIG. 2C, since the iris is roughly 500 microns thick at the pupil/iris boundary, the change in depth for features below the pupil plane occurs rather abruptly. Thus, in accordance with the present invention, FIG. 2C shows that the scan of OCT radiation provides an easily identifiable signature when the scan crosses the pupil/iris boundary.

Assuming the pupil to be circular, at least three, but preferably more, transverse scans of OCT radiation across the pupil/iris boundary are performed. The data from each scan are analyzed to determine spatial coordinates which represent the pupil/iris boundary. Such analysis entails determining a position at which there is a change in depth which exceeds a predetermined amount. Then, the spatial coordinates are used in accordance with geometrical methods which are well known in the art to determine the boundary of the pupil by, for example, fitting a circle through the spatial coordinates of the pupil boundary. Finally, the center of the pupil is determined in accordance with methods which are well known to those of ordinary skill in the art from the fitted circle. In accordance with one embodiment of the present invention, a raster-type scan is used, i.e., multiple horizontal scans, each scan extending completely across the pupil. However, in practice it is required that the measurements be completed in no more than, for example, $\frac{1}{10}$ of a second to avoid errors due to eye movement. Further, if the precise location of the eye is not known, the actual scan range should be several pupil diameters. These requirements, coupled with a mechanical limit on the maximum possible velocity of the reference scanner, may make it difficult to perform a raster scan quickly enough.

Figure 3:
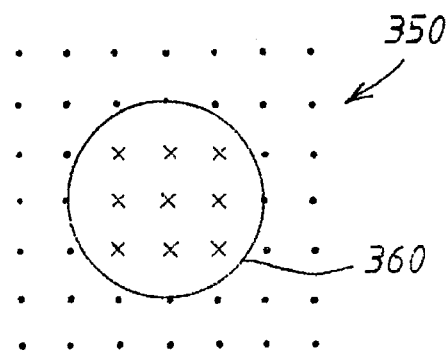
FIG. 3 shows, in pictorial form, a scan pattern of OCT radiation for acquiring data from an eye.

FIG. 3 shows, in pictorial form, a scan pattern of OCT radiation for acquiring data from an eye in an alternative embodiment of the present invention. In accordance with this alternative embodiment, a coarse-scan pattern consisting of a grid of points 350 is used to locate the pupil approximately. Depth information is collected at each point of grid 350. These data can be collected rather rapidly, even if the scan length of the reference path of OCT apparatus 30 is substantial. Except possibly when the eye is accommodating strongly, the depth of the center of the eye lens is such that it is below the iris. In accordance with the present invention, the depth of the points in measurement grid 350 are examined to identify a set of neighboring points which have a greater depth than that of surrounding points. As shown in FIG. 3, crosses indicate depths approximately 300–500μ below that of the surrounding tissue. In accordance with the present invention, the set of neighboring points within circle 360 locate the pupil to within an error equal to the grid spacing. The pupil, and its edge, are located, for example, by fitting a circle to encompass the set of neighboring points. Then, having located the pupil and its edge, a second set of short, linear scans of OCT radiation are made in the region of the pupil edge only, with preferably a reduced range for scan length of the reference path in OCT apparatus 30. This alternative embodiment is advantageous in that it reduces the total scan time substantially.

In another embodiment of the present invention, gaze tracking is performed by locating features on the fundus of eye 11. In this embodiment, an additional lens is needed to focus the scanning spot onto the retina. Two easily identifiable features are the papilla (the optic nerve head) and the foveola (the pit in the center of the fovea). Both of these features are characterized by significant (hundreds of microns) depth differences compared with surrounding tissue and can be found readily by a scan of OCT radiation in the manner described above. In this embodiment, as the eye rotates, i.e., changes its gaze angle, a given feature on the fundus moves a distance determined by the eyeball radius. Specifically, the change in gaze angle is given by:

$$\sin \theta = D/R \tag{1}$$

where $\theta$ is the gaze angle, D is the distance the given feature moves, and R is the eyeball radius. In practice, $\theta$ and D are related by a calibration procedure in which the subject eye fixates in a known direction and then fixates in a second known direction. Then, $\theta$ is given as the angle between the two known directions and D is measured. From this, a calibration for eqn (1) is readily determined as a scale factor for D. In accordance with such an embodiment of the present invention, a two-dimensional grid is scanned to search for these features. In order to provide an appropriately sized grid, the grid spacing used should be no more than ¼ to ½ of the lateral size of the features to be located. As those of ordinary skill in the art readily appreciate, the present invention is not limited to use of the papilla and the foveola and may include other identifiable features such as, for example, a distinctive pattern of blood vessels.

Referring back to FIG. 1, light source 63 outputs radiation having a wavelength which is different from the wavelength of the OCT radiation, for example, a light emitting diode. Radiation from light source 63 is reflected by 50—50 beamsplitter 50 towards eye 11. The light from source 63 is: (a) imaged by the cornea of eye 11, acting as a convex spherical mirror; (b) reflected by beamsplitter 50; (c) focused by focusing lens 62; and (d) detected by detector 61, for example, a video camera. In accordance with the present invention, focusing lens 62 focuses the pupil plane of eye 11 onto detector 61. Then, an output image from video camera 61 is applied as input to computer 70. The image from video camera 61 includes an image of radiation from light source 63 which was reflected from the cornea of eye 11. The image of the reflected radiation appears in the video image as a bright point of light which is referred to as the corneal reflex. The location and center of the corneal reflex is determined by computer 70 in accordance with methods which are well known in the art. In accordance with the present invention, light source 63 may be made sufficiently bright that it will also serve to illuminate the pupil plane of eye 11. Then, in accordance with the present invention, when detector 61 is a video camera, its output will show a pupil image as well as the corneal reflex (a typical LED for use in fabricating embodiments of the present invention would illuminate an area approximately one inch in diameter at a distance of approximately one foot).

Arrow 12 shown in FIG. 1 shows a fixation direction of eye 11. For example, in a clinical setting a patient would be asked to focus on light source 73 which is situated on a line that is coincident with the direction of arrow 12. Light from source 73 can be seen as it passes through beamsplitters 50 and 40.

As is known in the prior art, a change in the relative separation of the center of the corneal reflex and the center of the pupil is a measure of a change in gaze direction. In particular, the relationship of gaze angle to the location of the corneal reflex and the center of the pupil is given by the following formulae:

$$\sin \theta_x = (x_{cr} - x_p)/(A-a) \tag{2}$$

$$\sin \theta_y = (y_{cr} - y_p)/(A-a) \tag{3}$$

where $(\theta_x, \theta_y)$ are angles of eye rotation produced by changes in x and y, respectively; $(x_{cr}, y_{cr})$ are the x and y coordinates, respectively, of the location of the center of the corneal reflex; $(x_p, y_p)$ are the x and y coordinates, respectively, of the location of the center of the pupil; and $[(x_{cr}-x_p), (y_{cr}-y_p)]$ are the distances in x and y, respectively, between the two centers; A is the distance from the center of rotation of eye 11 to the outer corneal surface (~13.3 mm); and a is the radius of curvature of the outer surface of the cornea~8 mm.

Since the center of the corneal reflex and the center of the pupil are measured by different detector systems, it is important to calibrate each system to the same distance scale. In other words, it is necessary to know what change in the rotation angle of mirrors 33 produces a given millimeter change in OCT radiation spot position at eye 11 and what change in the position of the corneal reflex image at detector 61 corresponds to the same millimeter change in the location of the corneal reflex at the eye. This calibration is done experimentally or by calculation, in accordance with methods which are well known to those of ordinary skill in the art, knowing the lens focal lengths and spacings. Also, note that, only changes in the relative separation between the center of the corneal reflex and the center of the pupil are meaningful in eqns (2) and (3). As a result, it is necessary to calibrate the entire system for a patient's eye. In practice, since the properties of a given eye may not be precisely known, $\theta$ and the distance between the two centers of eqn (2) and (3) are related by a calibration procedure in which the subject eye fixates in a known direction and then fixates in a second known direction. Then, for each of eqn (2) and (3), $\theta$ is given as the angle between the two known directions and the distance between the two centers is measured. From this a calibration for eqns (2) and (3) is readily determined as a scale factor for the distance between the two centers.

Figure 4:
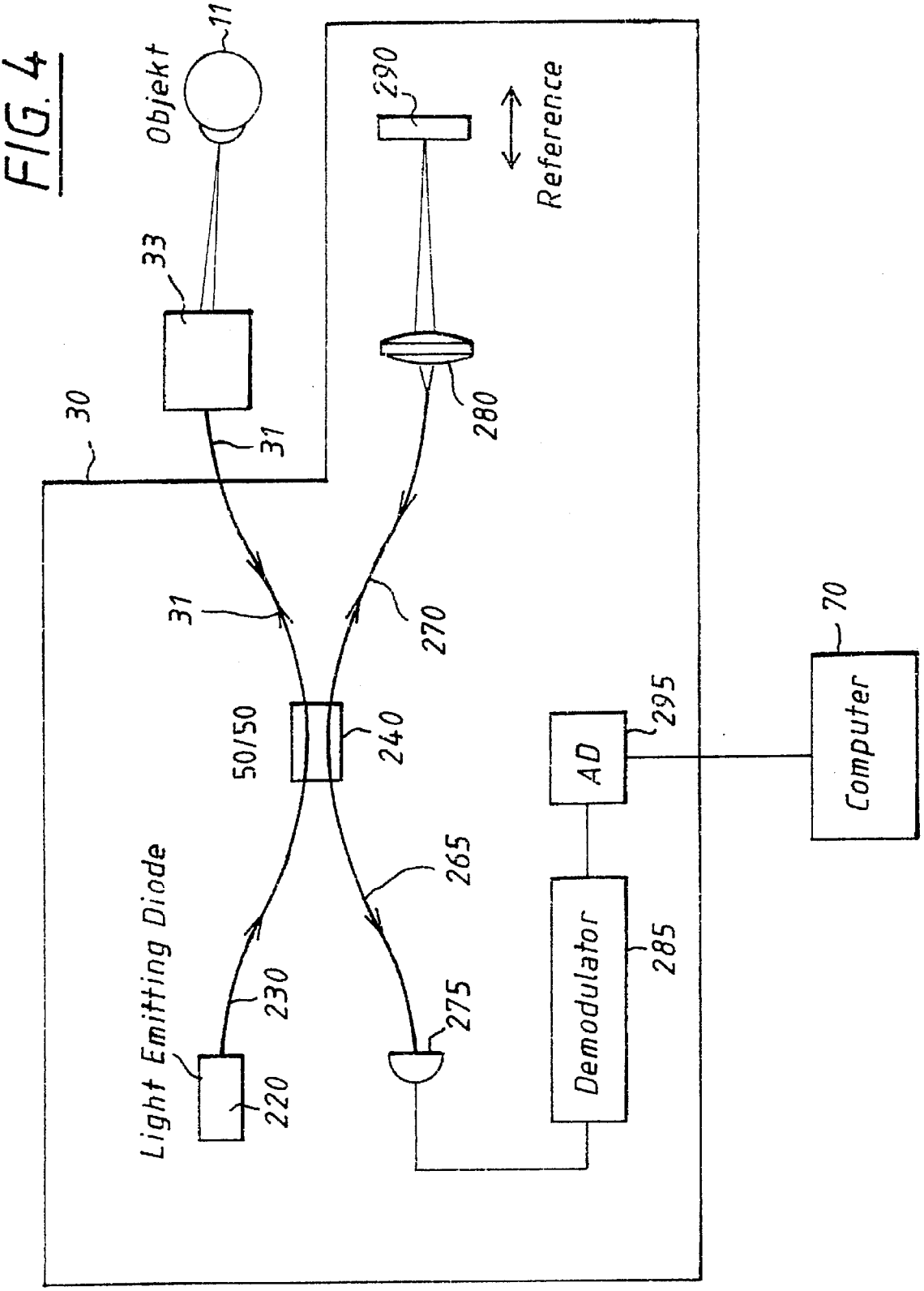
FIG. 4 shows, in pictorial form, a fiber optic embodiment of the OCT apparatus shown in FIG. 1.

FIG. 4 shows, in pictorial form, a fiber optic embodiment of OCT apparatus 30. As shown in FIG. 4, OCT apparatus 30 comprises CW radiation source 220, for example, a superluminescent laser diode having an output centered substantially at 850 nm. Output from source 220 is coupled into optical fiber 230 and is separated into two beams by 50/50 coupler 240. The output from 50/50 coupler 240 is coupled into optical fibers 31 and 270, respectively. The output from fiber 270 is imaged by lens 280 onto reference mirror 290 and output from fiber 31 is directed to transverse scanning apparatus 33. The output from transverse scanning apparatus 33 is directed to impinge upon eye 11 in the manner described in detail above. Then, radiation reflected from eye 11 is coupled back into fiber 31 and superimposed by 50/50 coupler 240 with radiation reflected from reference mirror 290 and coupled back into fiber 270. Superimposed radiation output from 50/50 coupler 240 is coupled into fiber 265. As is known, there is interference between radiation reflected from the eye 11 and radiation reflected from reference mirror 290 (the reference path) if the optical path difference is smaller than a length corresponding to the temporal coherence length of radiation source 220. Reference mirror 290 is moved with a substantially constant velocity by means which are well known to those of ordinary skill in the art (not shown) and, as a result, the interference is detected as a periodic variation of a detector signal obtained by photodetector 275, the periodic variation having a frequency equal to a Doppler shift frequency which is introduced by moving reference mirror 290 with the constant velocity. The output from photodetector 275 is demodulated by demodulator 285, the demodulated output from demodulator 285 is convened to a digital signal by analog-to-digital converter 295 (A/D 295), and the output from A/D 295 is applied as input to computer 70 for analysis. The signal input to computer 70 is bandpass filtered and the output from the bandpass filter is an oscillating signal pulse with a typical frequency of about 100 kHz and a pulse length which corresponds to the coherence length of light source 220. The output from the bandpass filter is further filtered, for example, by a root mean square filter to obtain the envelope of the signal pulse produced by photodetector 275. Next, an output signal from the root mean filter is applied as input to a trigger unit, for example, a Schmitt trigger, to derive a timing signal from the output of the root means filter. The timing pulse is used to store the position of reference mirror 290 at the moment of the trigger pulse. The position of mirror 290 corresponds to the length of the reference path which is equal to the optical path length of the sample beam. The interference signal vanishes as soon as the optical path difference between radiation reflected from the object and radiation reflected from reference mirror 290 becomes larger than a length corresponding to the temporal coherence length of source 220.

Those skilled in the art will recognize that the foregoing description has been presented for the sake of illustration and description only. As such, it is not intended to be exhaustive or to limit the invention to the precise form disclosed. For example, modifications and variations are possible in light of the above teaching which are considered to be within the spirit of the present invention. Thus, it is to be understood that the claims appended hereto are intended to cover all such modification and variations which fall within the true scope and spirit of the invention.

What is claimed is:

1. Apparatus for gaze tracking an eye which comprises:
   an optical coherence tomography (OCT) apparatus that generates optical output and generates detection signals in response to backscattered optical output;
   a scanner that scans the optical output along one or more trajectories across a predetermined portion of the eye and transfers to the OCT apparatus portions of optical output backscattered from materials in the eye;
   a depth analyzer that analyzes the detection signals at various positions along the one or more trajectories to determine depths in the eye of the materials that backscattered the optical output;
   a location analyzer, responsive to the depths, that determines a location of a feature of the eye;
   an illuminator which produces a reflection of radiation from a cornea of the eye (corneal reflex);
   a detector which determines a location of the corneal reflex; and
   a gaze tracker, responsive to the location of the feature and to the location of the corneal reflex, which tracks the gaze.

2. The apparatus of claim 1 wherein the feature is a pupil and the location of the feature is a center of the pupil.

3. The apparatus of claim 2 wherein the location analyzer further determines:

$\sin \theta_x = (x_{cr} - x_p)/(A-a)$ and $\sin \theta_y = (y_{cr} - y_p)/(A-a)$ where $(\theta_x, \theta_y)$ are measures of change in gaze direction in x and y, respectively, $(x_{cr} - x_p)$ and $(y_{cr} - y_p)$ are distances in x and y, respectively, between the center of the corneal reflex and the center of the pupil; A is a calibrated distance from a center of rotation of the eye to an outer corneal surface and a is calibrated radius of curvature of the outer surface of the cornea.

4. The apparatus of claim 1 wherein the location analyzer determines locations at which depth in the eye of material at positions along a trajectory are different by a predetermined amount from depth in the eye of material at other positions along the trajectory.

5. The apparatus of claim 4 wherein the predetermined portion of the eye includes a pupil/iris boundary.

6. The apparatus of claim 4 wherein:
   the scanner scans the optical output along trajectories that cross a pupil/iris boundary at least three times; and
   the location analyzer determines at least three locations on the pupil/iris boundary.

7. The apparatus of claim 6 wherein the location analyzer further comprises a center finder which determines a center of the pupil from the locations on the pupil/iris boundary.

8. The apparatus of claim 4 wherein the location analyzer determines locations at which amplitude of the detection signals exceed a predetermined amount.

9. Apparatus for gaze tracking an eye which comprises:
   on optical coherence tomography (OCT) apparatus that generates optical output and generates detection signals in response to backscattered optical output;
   a scanner, in response to coarse scan commands from a controller, that coarse scans the optical output over a two-dimensional grid which encompasses at least a portion of a pupil/iris boundary and transfers to the OCT apparatus portions of optical output backscattered from materials in the eye;
   a depth analyzer that analyzes detection signals from the coarse scan at various positions over the grid to determine depths in the eye of the materials that backscattered the optical output;
   a location analyzer, responsive to the depths from the coarse scan, that determines a coarse pupil/iris boundary;
   wherein the scanner, in response to fine scan commands from the controller, fine scans the optical output along one or more trajectories across the coarse pupil/iris boundary and transfers to the OCT apparatus portions of optical output backscattered from materials in the eye;
   wherein the depth analyzer analyzes detection signals from the fine scan at various positions along the one or more trajectories to determine depths in the eye of the materials that backscattered the optical output; and
   wherein the location analyzer, responsive to the depths from the fine scan, determines the center of the pupil.

10. Apparatus for gaze tracking an eye which comprises:
    an optical coherence tomography (OCT) apparatus that generates optical output and generates detection signals in response to backscattered optical output;
    a scanner that scans the optical output along one or more trajectories across a predetermined portion of the eye and transfers to the OCT apparatus portions of optical output backscattered from materials in the eye;
    a depth analyzer that analyzes the detection signals at various positions along the one or more trajectories to determine depths in the eye of the materials that backscattered the optical output:

a location analyzer, responsive to the depths, that determines a location of a feature on a fundus of the eye; and a gaze tracker, responsive to the location of the feature, that tracks the gaze.

11. The apparatus of claim 10 wherein the location analyzer determines locations at which depth in the eye of material at positions along a trajectory are different by a predetermined amount from depth in the eye of material at other positions along the trajectory.

12. The apparatus of claim 11 wherein the location analyzer further determines sin θ32 D/R where θ is a measure of change of gaze direction, D is a calibrated distance the feature moves, and R is a radius of the eyeball.

13. The apparatus of claim 11 wherein the feature is one of a foveola and a papilla.

14. The apparatus of claim 11 wherein the feature is a pattern of blood vessels.

15. Apparatus for gaze tracking an eye which comprises:

an optical coherence tomography (OCT) apparatus that generates optical output and generates detection signals in response to backscattered optical output:

a scanner that scans the optical output over a two-dimensional grid which encompasses a feature, the grid having a spacing which is smaller than a size of the feature and transfers to the OCT apparatus portions of optical output backscattered from materials in the eye;

a depth analyzer that analyzes detection signals from the scan at various positions over the grid to determine depths in the eye of materials that backscattered the optical output;

a location analyzer, responsive to the depths from the scan, that determines a location of the feature.

16. A method for gaze tracking an eye which comprises the steps of:

scanning radiation output from an optical coherence tomography (OCT) apparatus along one or more trajectories across a predetermined portion of the eye and transferring to the OCT apparatus portions of optical output backscattered from materials in the eye;

analyzing detection signals output from the OCT apparatus in response to the backscattered optical output at various positions along the one or more trajectories to determine depths in the eye of materials that backscattered the optical output:

determining a location of a feature of the eye from the depths;

illuminating the eye to produce a reflection of radiation from a cornea of the eye (corneal reflex);

detecting a location of the corneal reflex; and gaze tracking in response to the location of the feature and to the location of the corneal reflex.

17. Apparatus for gaze tracking an eye which comprises:

an optical coherence tomography (OCT) apparatus that generates optical output and generates detection signals in response to backscattered optical output;

a scanning means for scanning the optical output along one or more trajectories across a predetermined portion of the eye and for transferring to the OCT apparatus portions of optical output backscattered from materials in the eye;

a depth analyzer means for analyzing the detection signals at various positions along the one or more trajectories to determine depths in the eye of materials that backscattered the optical output;

a location analyzer means, responsive to the depths, for determining a location of a feature of the eye;

illumination means for producing a reflection of radiation from a cornea of the eye (corneal reflex);

detecting means for determining a location of the corneal reflex; and a gaze tracker means, responsive to the location of the feature and to the location of the corneal reflex, for gaze tracking.

18. The apparatus of claim 17 wherein the feature is a feature on the fundus.

19. Apparatus for gaze tracking an eye which comprises:

an optical coherence tomography (OCT) apparatus that generates optical output and generates detection signals in response to backscattered optical output;

a scanner means, in response to commands from a controller, for scanning the optical output over a two-dimensional grid that encompasses a feature and for transferring to the OCT apparatus portions of the optical output backscattered from materials in the eye;

a depth analyzer means for analyzing the detection signals at various positions over the grid to determine depths in the eye of materials that backscattered the optical output; and a location analyzer means, responsive to the depths, for determining a location of the feature.

20. The apparatus of claim 19 wherein:

location analyzer means comprises boundary means for determining a coarse feature boundary;

wherein the scanning means, responsive to fine scan commands from the controller, comprises means for scanning the optical output along one or more trajectories across the coarse feature boundary and for transferring to the OCT apparatus portions of the optical output backscattered from materials in the eye;

wherein the depth analyzer means further comprises fine depth analyzer means, for analyzing detection signals from the fine scan at various positions along the one or more transverse trajectories to determine depths in the eye of materials that backscattered the optical output; and;

wherein the location analyzer means further comprises means, responsive to the depths from the fine scan, for determining the location of the feature.

* * * * *